United States Patent
Speier

(10) Patent No.: US 10,175,310 B2
(45) Date of Patent: Jan. 8, 2019

(54) DETERMINING A MEASURING POINT-IN-TIME IN A CARDIAC CYCLE FOR CONDUCTING MAGNETIC RESONANCE DIFFUSION MEASUREMENTS

(71) Applicant: Siemens Aktiengesellschaft, Munich (DE)

(72) Inventor: Peter Speier, Erlangen (DE)

(73) Assignee: Siemens Aktiengesellschaft, Munich (DE)

(*) Notice: Subject to any disclaimer, the term of this patent is extended or adjusted under 35 U.S.C. 154(b) by 989 days.

(21) Appl. No.: 14/631,013

(22) Filed: Feb. 25, 2015

(65) Prior Publication Data

US 2015/0241526 A1  Aug. 27, 2015

(30) Foreign Application Priority Data

Feb. 26, 2014  (DE) .................. 10 2014 203 431

(51) Int. Cl.
*G01R 33/28* (2006.01)
*A61B 5/02* (2006.01)
(Continued)

(52) U.S. Cl.
CPC ........ *G01R 33/281* (2013.01); *A61B 5/02028* (2013.01); *G01R 33/448* (2013.01);
(Continued)

(58) Field of Classification Search
CPC ................ G01R 33/281; G01R 33/448; G01R 33/4828; G01R 33/56341; G01R 33/56509; A61B 5/02028
See application file for complete search history.

(56) References Cited

U.S. PATENT DOCUMENTS 8,878,838 B2 * 11/2014 Hautvast ............... G06T 7/0012
345/418
8,897,519 B2 * 11/2014 Guhring ............... A61B 5/0263
382/128

(Continued)

OTHER PUBLICATIONS

Dou et al. "Cardiac Diffusion MRI Without Motion Effects", Magnetic Resonance in Medicine, 2002, vol. 48, pp. 105-114; (2002).

(Continued)

*Primary Examiner* — Dixomara Vargas
(74) *Attorney, Agent, or Firm* — Schiff Hardin LLP

(57) ABSTRACT

In a method and magnetic resonance (MR) system for determining at least one measuring point-in-time in a cardiac cycle for conducting diffusion measurements of the myocardium of an examination object, a sequence of MR images of the heart is acquired and a time curve of a parameter of the cardiac geometry is determined in the sequence of MR images. At least one mean of the parameter of the cardiac geometry is determined from the time curve of the parameter. For the determined at least one mean of the parameter, the associated point-in-time in the time curve of the parameter is determined in which the determined mean occurs, wherein the determined point-in-time defines the at least one measuring point-in-time in a cardiac cycle during which the diffusion measurements of the myocardium are carried out.

12 Claims, 7 Drawing Sheets

(51) Int. Cl.
*G01R 33/44* (2006.01)
*G01R 33/48* (2006.01)
*G01R 33/563* (2006.01)
*G01R 33/565* (2006.01)

(52) U.S. Cl.
CPC ... *G01R 33/4828* (2013.01); *G01R 33/56341* (2013.01); *G01R 33/56509* (2013.01)

(56) References Cited

U.S. PATENT DOCUMENTS

| | | | | |
|---|---|---|---|---|
| 9,345,436 | B2* | 5/2016 | Hunziker | A61B 5/7278 |
| 9,545,206 | B2* | 1/2017 | Miyazaki | G01R 33/56366 |
| 9,585,575 | B2* | 3/2017 | Miyazaki | G01R 33/56366 |
| 9,949,696 | B2* | 4/2018 | Goedje | A61B 5/028 |
| 2006/0241379 | A1 | 10/2006 | Greiser et al. | |
| 2011/0285702 | A1* | 11/2011 | Hautvast | G06T 7/0012 |
| | | | | 345/419 |
| 2014/0050379 | A1* | 2/2014 | Miyazaki | G01R 33/56366 |
| | | | | 382/131 |
| 2014/0194730 | A1* | 7/2014 | Hoshino | A61B 5/0044 |
| | | | | 600/419 |
| 2014/0275937 | A1* | 9/2014 | Goedje | A61B 5/028 |
| | | | | 600/399 |
| 2014/0276071 | A1* | 9/2014 | Hunziker | A61B 5/7278 |
| | | | | 600/453 |
| 2015/0192653 | A1* | 7/2015 | Sharif | A61B 5/055 |
| | | | | 600/420 |
| 2015/0216429 | A1* | 8/2015 | Miyazaki | G01R 33/56366 |
| | | | | 600/419 |
| 2016/0296178 | A1* | 10/2016 | Korporaal | G06T 7/0016 |
| 2016/0324427 | A1* | 11/2016 | Meyer | A61B 5/0263 |

OTHER PUBLICATIONS

Edelman et.al. :"In vivo measurement of water diffusion in the human heart", : Magn Reson Med., vol. 32(3):423-8, (1994).

Tseng et.al. :"Cardiac Diffusion Tensor MRI In Vivo Without Strain Correction", Magnetic Resonance in Medicine, vol. 42, pp. 393–403, (1999).

Nielles-Vallespin et.al. :"In Vivo Diffusion Tensor MRI of the Human Heart: Reproducibility of Breath-Hold and Navigator-Based Approaches" Magnetic Resonance in Medicine, pp. 1–12, (2012).

McGill et.al. :"Reproducibility of in-vivo diffusion tensor cardiovascular magnetic resonance in hypertrophic cardiomyopathy", Journal of Cardiovascular Magnetic Resonance 14:86, (2012).

Rapacchi et.al. :"Low b-Value Diffusion-Weighted Cardiac Magnetic Resonance Imaging", Journal of Cardiovascular Magnetic Resonance 14:86, (2012).

Reese et.al. :"Imaging myocardial fiber architecture in vivo with magnetic resonance", Magnetic Resonance in Medicine, vol. 34(6), pp. 786-791, (1995).

* cited by examiner

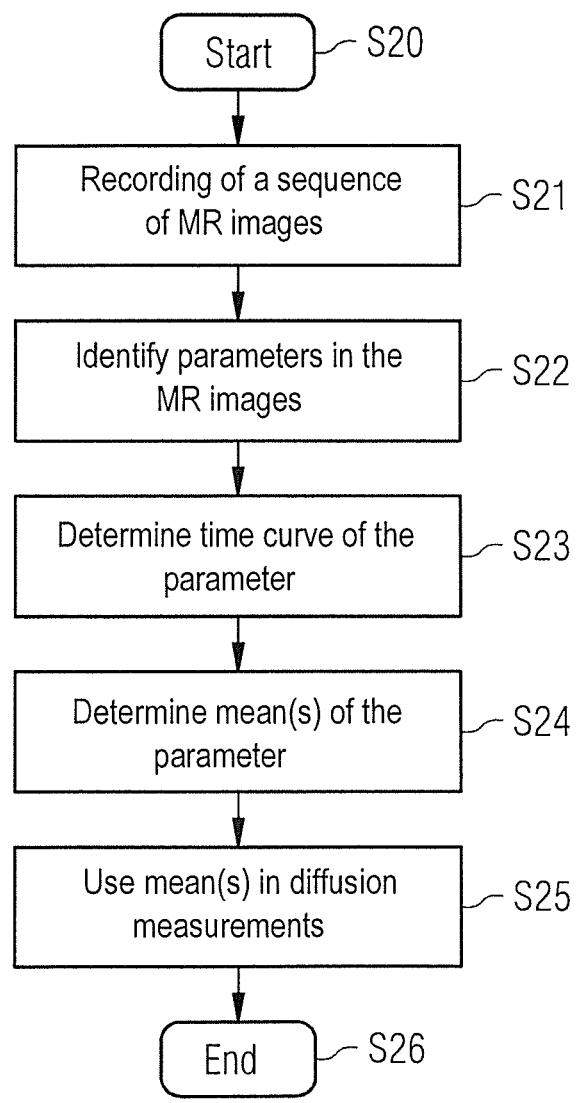

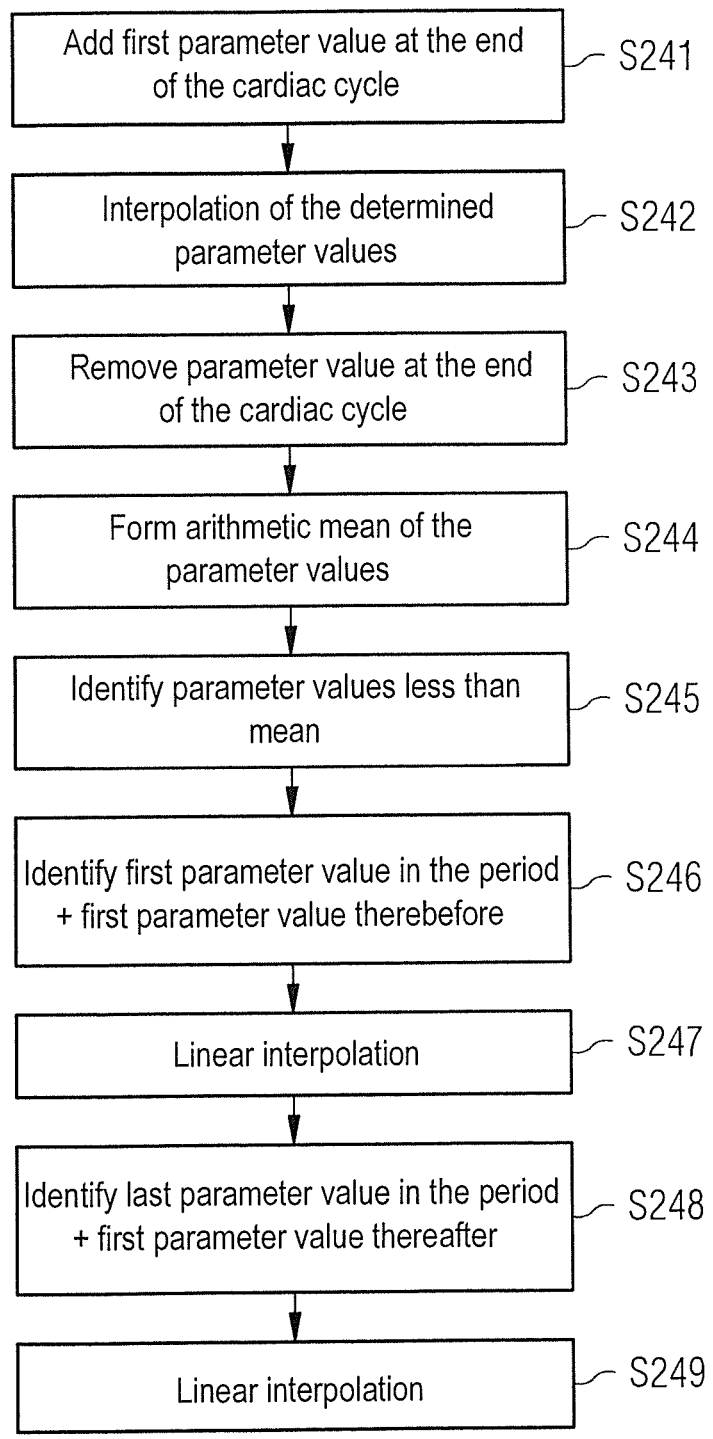

DETERMINING A MEASURING POINT-IN-TIME IN A CARDIAC CYCLE FOR CONDUCTING MAGNETIC RESONANCE DIFFUSION MEASUREMENTS

BACKGROUND OF THE INVENTION

Field of the Invention

The present invention relates to a method for determining at least one measuring point-in-time in a cardiac cycle that can be used for conducting diffusion measurements of the myocardium of an examination object in a magnetic resonance (MR) system. The invention also relates to an associated MR system and to an electronically readable data carrier (storage medium).

Description of the Prior Art

Magnet resonance tomography (MRT) is a versatile imaging modality because MR images of an examination object can be generated with many different contrasts. The contrasts that are usually used are contrasts based on relaxation mechanisms, such as the T1 time or T2 time. Either native tissue properties or contrast media-induced properties of the tissue are used in this connection. Further contrast possibilities are the use of flow effects, such as the inflow of nuclear spins that have been given a magnetization into an imaging plane, the phase development of flowing nuclear spins, magnetization transfer methods, and diffusion.

Diffusion-weighted imaging has recently been applied in various regions of the body. With Diffusion Tensor Imaging (DTI) the variation in the direction of the measured diffusion of the water in the tissue is measured and analyzed. The observed variations in diffusion are generated by the movement of the water molecules in the tissue region in the spatial direction of the diffusion encoding. The spatial dependency of the diffusion depends on the geometry of the tissue region and can be described by a diffusion tensor. A set of diffusion measurements having different encoding directions is used for measuring the tensor properties. One possible application of DTI is known as "Fiber Tracking", and this leads to a color depiction of the neuronal activity in the brain. DTI can be used in the heart to determine the geometry of the muscle cells in the myocardium. In a normal heart these cells are arranged in a helix structure, it being possible to depict the structure using DTI. The following documents are examples of this:

"In vivo measurement of water diffusion in the human heart," Edelman R R, Gaa J, Wedeen V J, Loh E, Hare J M, Prasad P, Li W., Magn Reson Med. 1994 September; 32(3):423-8

"Cardiac diffusion tensor MRI in vivo without strain correction," Tseng W Y, Reese T G, Weisskoff R M, Wedeen V J., Magn Reson Med. 1999 August; 42(2):393-403

"In vivo diffusion tensor MRI of the human heart: reproducibility of breath-hold and navigator-based approaches," Nielles-Vallespin S, Mekkaoui C, Gatehouse P, Reese T G, Keegan J, Ferreira P F, Collins S, Speier P, Feiweier T, de Silva R, Jackowski M P, Pennell D J, Sosnovik D E, Firmin D., Magn Reson Med. 2013 August; 70(2):454-65

"Reproducibility of in-vivo diffusion tensor cardiovascular magnetic resonance in hypertrophic cardiomyopathy," Laura-Ann McGill, Tevfik F Ismail, Sonia Nielles-Vallespin, Pedro Ferreira, Andrew D Scott, Michael Roughton, Philip J Kilner, S Yen Ho, Karen P McCarthy, Peter D Gatehouse, Ranil de Silva, Peter Speier, Thorsten Feiweier, Choukkri Mekkaoui, David E Sosnovik, Sanjay K Prasad, David N Firmin and Dudley J Pennell, Journal of Cardiovascular Magnetic Resonance 2012, 14:86

"Low b-value diffusion-weighted cardiac magnetic resonance imaging: initial results in humans using an optimal time-window imaging approach," Rapacchi S, Wen H, Viallon M, Grenier D, Kellman P, Croisille P, Pai V M., Invest Radiol. 2011 December; 46(12):751

In the case of one of these methods, a periodic intensity modulation is encoded in one spatial direction during a first heartbeat. During the period of one heartbeat this modulation is stored as a longitudinal magnetization, which relaxes with the T1 time, with the diffusion occurring in this period of the heartbeat blurring the modulation pattern. After this encoding step of the modulation, the spatial modulation is decoded by reversing the modulation. Changes in the spatial modulation over the period due to the diffusion produce a signal attenuation. The movement of the heart will also influence the modulation. Decoding consequently occurs exactly in the same cardiac phase as the encoding in the previous heartbeat. The cardiac geometry and movement is therefore the same in the case of encoding and decoding, and this identifies the diffusion as the single attenuation mechanism in the blurring of the modulation pattern. The diffusion can thus be measured. Since the respiratory movement also influences the pattern, this influence is eliminated by measuring with breath-hold techniques.

Assuming that encoding takes place during diastole when the heart muscle is relaxed, the heart muscle contracts during the systole, and this leads to a change in the region geometry. For example, the thickness of the myocardium wall of the left ventricle increases in the radial direction during the contraction, and the modulation pattern is stretched in this direction. The diffusion that occurs in the contracted state in this direction has a smaller effect than the diffusion that occurs when the heart muscle is relaxed.

This means that the tissue formation relative to the geometry during the encoding time during the cardiac cycle influences the signal attenuation, and this leads to an error in the diffusion measurement. If the tissue is compressed the signal attenuation is intensified by diffusion, whereas the signal attenuation is reduced in one direction by diffusion if the tissue is pulled apart in this direction between encoding and decoding.

It is therefore necessary to reduce the influence of the compression or expansion in diffusion measurements. In order to obtain a diffusion measurement that is independent of the tissue deformation, it is therefore necessary to take into account the tissue deformation such as expansion or compression. This may be done in two ways:

1. The three-dimensional deformation pattern is measured during the cardiac cycle, and the measured attenuation corrected with the use of this data. A method of this kind is described in "Imaging myocardial fiber architecture in vivo with magnetic resonance," Reese T G, Weisskoff R M, Smith R N, Rosen B R, Dinsmore R E, Wedeen V J. Magn Reson Med. 1995 December; 34(6):786-91.

Complex tagging methods or phase contrast measurements are required for measuring the deformation.

2. The distortion pattern is again measured during the cardiac cycle. The measurement is made in what is known as a sweet spot as the deformation effect is cancelled out. It was found in the document mentioned last that all deformation components vary roughly synchronously with time and that the diffusion varies roughly linearly with the deformation.

According to these requirements two sweet spots exist in a cardiac cycle. If the encoding and decoding of the diffusion are carried out so as to be coordinated with the point-in-times of the sweet spots then the measurement is independent of the deformation.

The methods mentioned above, however, are all complicated or time-consuming, however.

SUMMARY OF THE INVENTION

The methods mentioned above are all complicated or time-consuming.

An object of the present invention is to easily determine the sweet spot or measuring point-in-time that is suitable for diffusion measurements of the myocardium.

This object is achieved in accordance with the invention by a method for determining at least one measuring point-in-time in a cardiac cycle for conducting diffusion measurements of the myocardium of an examination object in an MR system, wherein a sequence of MR images of the heart is recorded, and wherein a time curve of a parameter of the cardiac geometry in the sequence of MR images is also determined. At least one mean of the parameter is determined from the determined time curve of the parameter of the cardiac geometry. For the determined at least one mean of the parameter the associated point-in-time in the time curve of the parameter is determined in which the at least one mean occurs. The determined point-in-time defines the at least one measuring point-in-time in a cardiac cycle during which the diffusion measurement of the myocardium is carried out.

According to the invention the additional deformation measurements of the tissue can be omitted and the sweet spot/measuring point-in-time can be easily determined. The measuring point-in-time, which corresponds to the sweet spot for the diffusion measurement, is determined by simple observation of the time curve and the averaging. Since the spatial mean of the parameter of the cardiac geometry denotes that just as much movement occurs in one direction as in the opposite one, the deformation-induced influence averages itself out on the diffusion measurements. If the diffusion measurement is carried out during the measuring point-in-time(s) determined in this way, the diffusion measurement is substantially independent of tissue contractions or tissue expansions over the cardiac cycle. The parameter of the cardiac geometry is preferably connected to the blood volume around which the myocardium flows. The point-in-time in a cardiac cycle in which the diffusion measurements can be carried out can be defined from the time-volume curves, without taking into account and/or quantifying the tissue compression or expansion.

A parameter value belonging to an MR image is preferably determined in the sequence of MR images, with an arithmetic mean of the parameter values being determined and the point-in-time, belonging to the arithmetic mean, in the time curve of the parameter at which the parameter matches the arithmetic mean. This point-in-time belonging to the arithmetic mean is then the at least one measuring point-in-time during which the diffusion measurements can be carried out.

It is also possible for the determination of the at least one measuring point-in-time to determine a period in the time curve of the parameter during which all determined parameter values are smaller than the mean. Within this period the determined first parameter is identified and the parameter determined directly therebefore in the time curve and the respectively associated point-in-times, which will be called first point-in-times hereinafter. The first measuring point-in-time for conducting the diffusion measurement accordingly lies between the two determined first point-in-times. A second measuring point-in-time can be determined with the aid of the last parameter value within the period and the parameter value determined directly thereafter in the time curve. The second measuring point-in-time, which lies between these two associated second point-in-times, can then be determined from the respectively associated point-in-times in the time curve, the second point-in-times.

Since the heart contracts during a cardiac cycle, the volume is always greater at the beginning and end of the cycle than the mean. Since there is only one contraction per cardiac cycle, the determined measured values form a connected interval. By determining the first and second point-in-times the measuring point-in-time at which a diffusion measurement can preferably be carried out can be determined by way of example by linear interpolation between the respective first point-in-times or by a linear interpolation between the second point-in-times. The parameter of the cardiac geometry can be by way of example the length of the endocardial contour of the myocardium, the epicardial contour of the myocardium, the myocardium volume or the blood volume surrounded by the myocardium. Other gauges are conceivable, such as the area enclosed by the contour, the maximum or minimum radius, etc. These parameters can be identified in the individual MR images by segmenting, and the change over time in one of these parameters can be used to identify the sweet spot/measuring point-in-time with the associated arithmetic mean.

The sequence of MR images can be generated for example, with a gradient echo sequence in which the used magnetic field gradients are all completely refocused. The sequence of these MR images can be depicted in what is known as a cine mode in which the cardiac cycle runs through like a film.

The parameter of the cardiac geometry is determined by way of example by identifying the parameter in each MR image of the sequence of MR images. A single imaging layer of the heart can be used in this connection, so each MR image depicts a single imaging layer of the heart and the sequence of MR images depicts the time curve in a single layer of the heart. Of course it is also possible to use a number of imaging layers to determine the time curve of the parameter.

The parameter value determined first in the time curve can also be added at the end of the cardiac cycle so there is a cyclical movement which begins and ends at the same location, and this is conventionally the case in a cardiac cycle. The parameter determined first in the time curve can be added at the end of the cardiac cycle before an interpolation between the parameters is carried out from the sequence of MR images and the parameters determined therein, in order to determine the time curve of the parameter. The parameter value added at the end of the cardiac cycle can be removed again before the averaging. In the case of the determined measuring point-in-times, the diffusion gradients can then be switched with which the diffusion is encoded during the subsequent diffusion measurements, and these are independent of the deformation geometry. The diffusion gradients can be situated, by way of example, centrally around the measuring point-in-times which were determined as described above.

The invention also relates to an MR system designed to carry out the method mentioned above, having an image recording unit for recording the sequence of MR images and an arithmetic unit designed to determine the mean of the parameter of the cardiac geometry, as described in detail above.

A non-transitory, electronically readable data carrier (storage medium) encoded with electronically readable control information is also encompassed by the invention. The control information causes the method described above to be implemented when the data carrier is headed in an arithmetic unit of an MR system.

BRIEF DESCRIPTION OF THE DRAWINGS

FIG. 2 is a flowchart with steps that can be carried out to determine the measuring point-in-times.

FIG. 3 is a flowchart that provides more details of the sub-steps of the flowchart of FIG. 2 in order to identify the measuring point-in-times.

DESCRIPTION OF THE PREFERRED EMBODIMENTS

Figure 1:
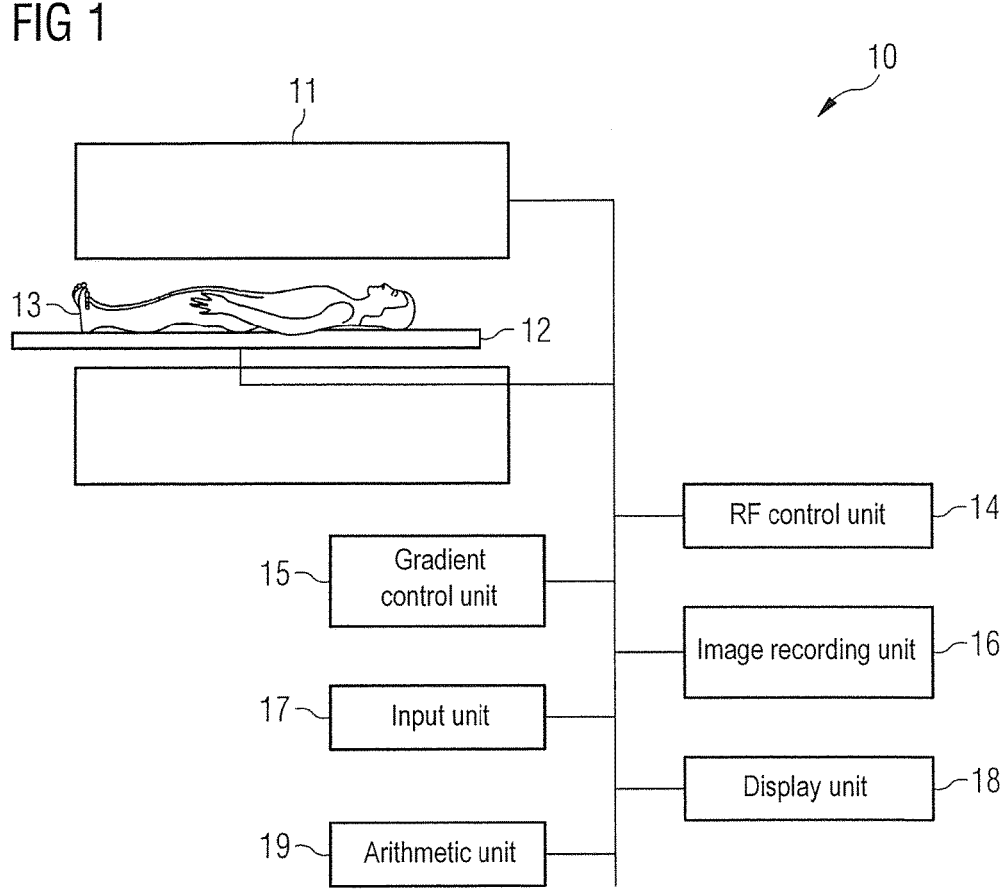
FIG. 1 schematically shows an MR system with which measuring point-in-times can be determined which can be used for diffusion measurements.
Figure 4A:
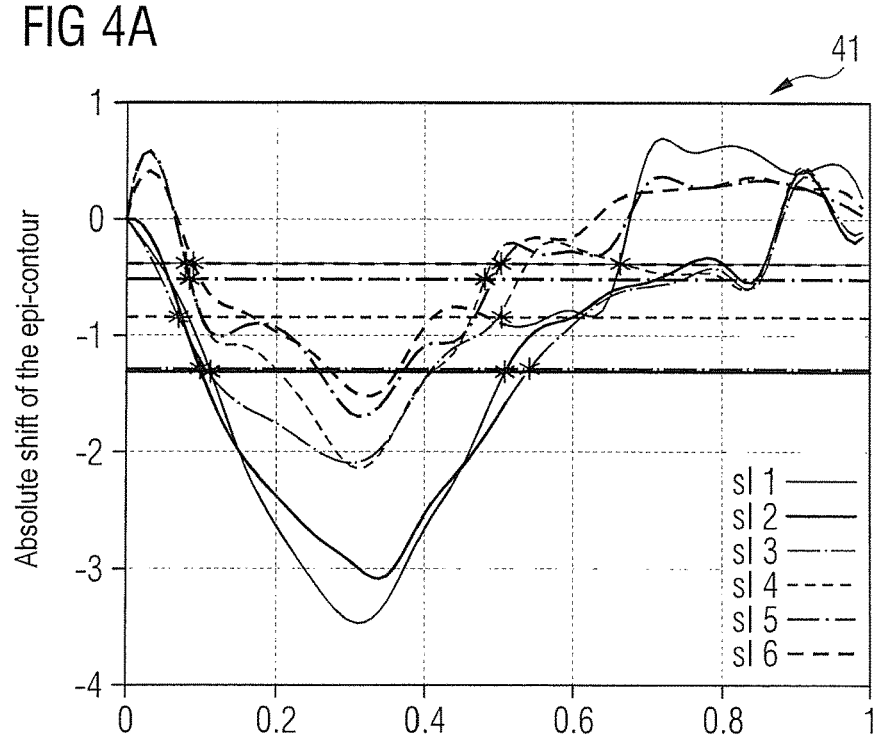
FIGS. 4A-4F respectively show time curves of different parameters of the cardiac geometry and the associated averaging.
Figure 4B:
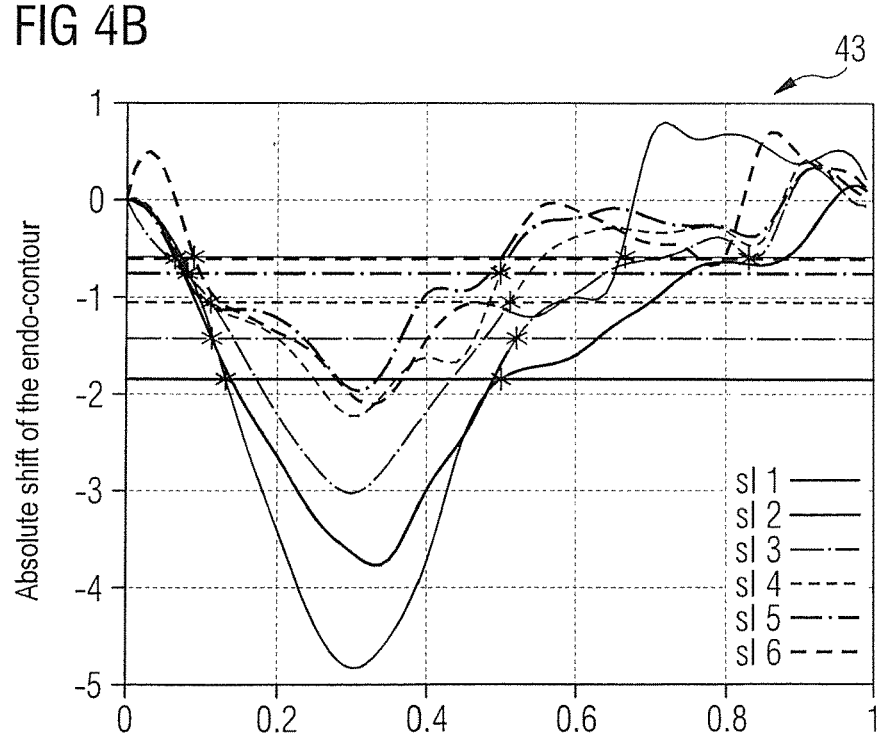
Figure 4C:
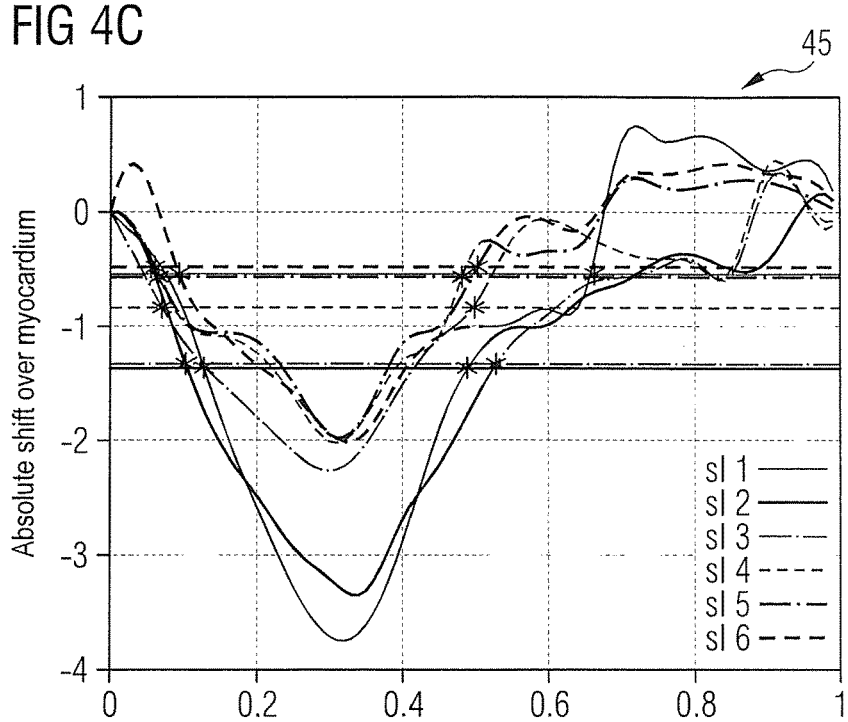
Figure 4D:
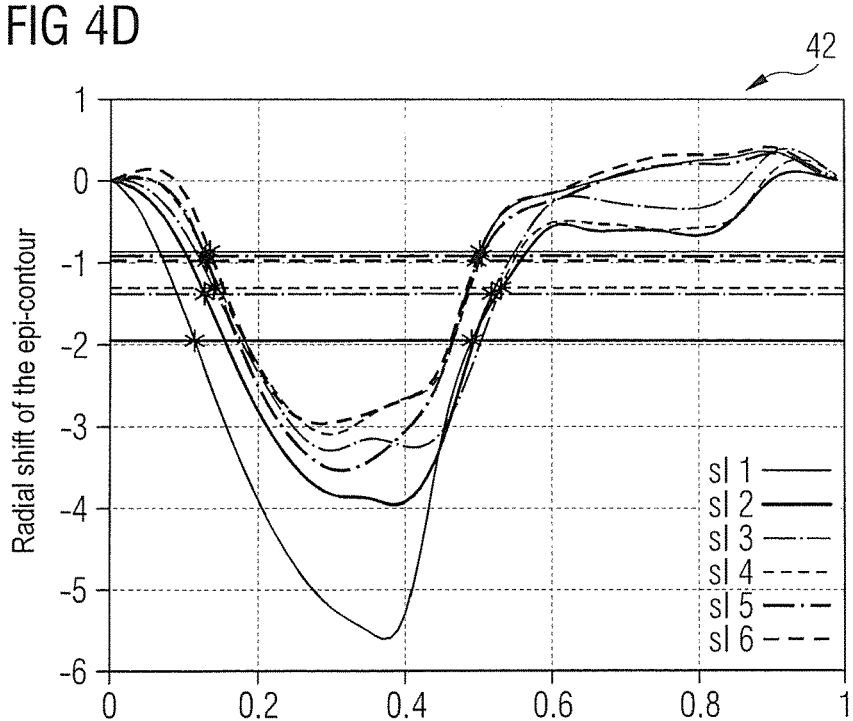
Figure 4E:
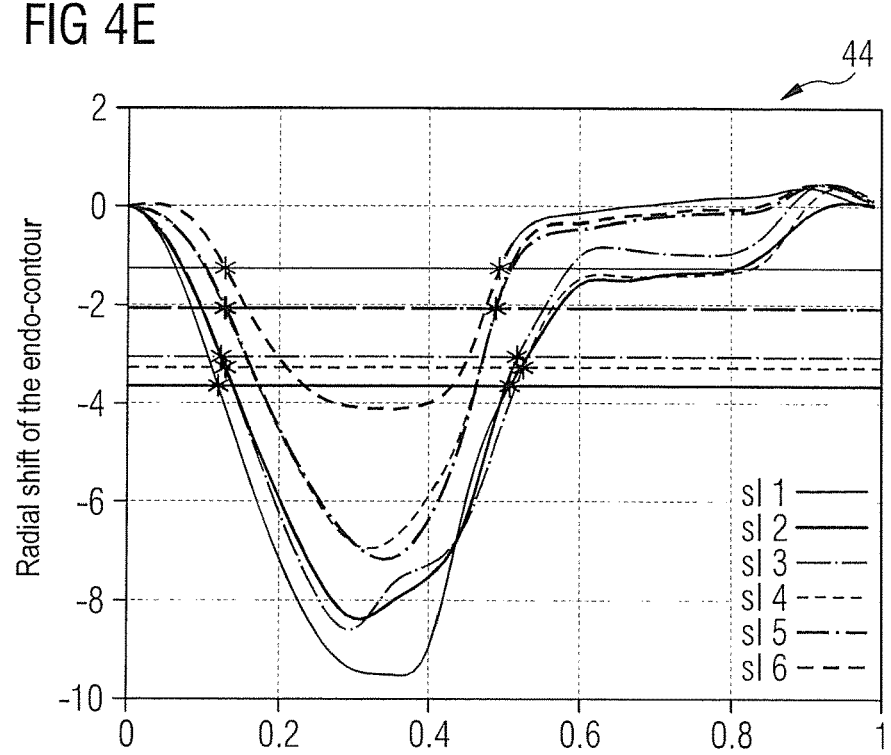
Figure 4F:
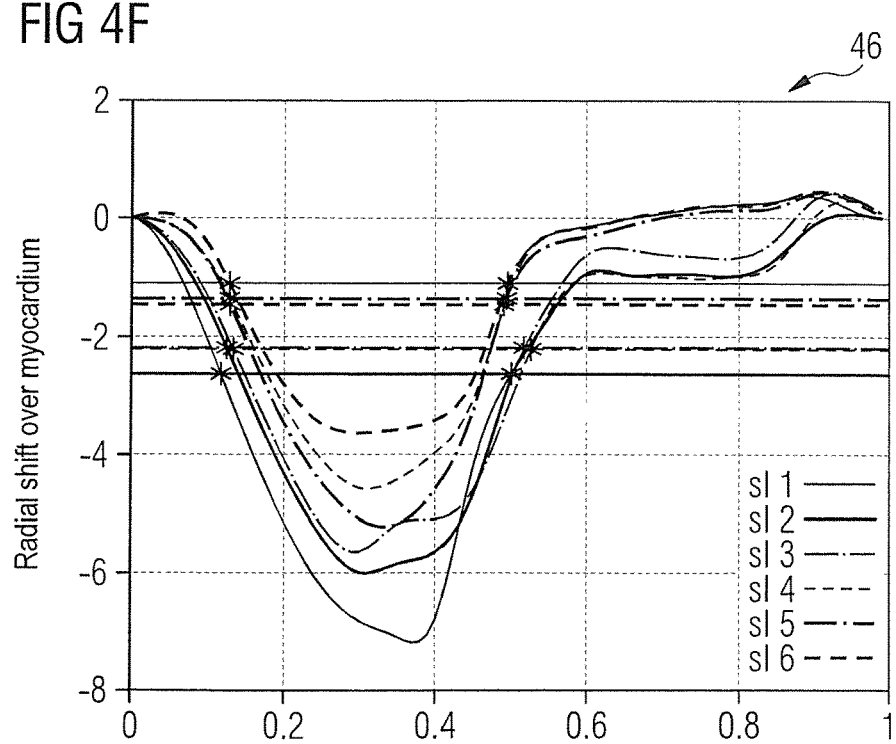

FIG. 1 schematically shows an MR system with which measuring point-in-times can be determined in a cardiac cycle. These are then used when conducting diffusion measurements of the myocardium to encode the diffusion. The MR system 10 has a magnet 11 for generating a polarization field B0. A person being examined 13 disposed on a couch 12 is located in a magnet 11, so a resulting magnetization is produced in the direction of the polarization field B0. Magnetic field gradients, which vary over time, for spatial encoding of the magnetization can be applied by magnetic field gradient coils (not shown). RF pulses can be emitted into the person being examined 13 by way of transmitting and/or receiving RF coils (not shown) to configure the magnetization, and the resulting transversal magnetization can be detected by the one or more transmitting-receiving coil(s). An RF control unit 14 is provided for generating the RF pulses which are emitted into the person being examined. A gradient control unit 15 controls the switching of the magnetic field gradients. An image recording unit 16 determines as a function of the chosen imaging sequence with which sequence over time the RF pulses and magnetic field gradients are applied and thereby controls inter alia the gradient control unit 13 and RF control unit 14. An operator of the MR system 10 can operate the MR system, choose imaging sequences, determine imaging planes, etc. by way of an input unit 17. The generated MR images can be displayed on a display unit 18. An arithmetic unit 19 can calculate the MR images from the detected signals. As described in detail below, the arithmetic unit can also determine from a sequence of MR images, which were obtained of the heart of the person being examined 13, measuring point-in-times which correspond to what are known as the sweet spots. These sweet spots can be used for diffusion measurements, such as tensor-based diffusion measurements, in order to switch (activate) the different diffusion gradients during these measuring point-in-times, which gradients are necessary for encoding the diffusion in the different spatial directions.

FIG. 2 shows steps of a method with which these measuring point-in-times or sweet spots may be identified. After the start of the method in step S20 a sequence of MR images is recorded in step S21. MR images of the short heart axis can be recorded in this connection with the use of a gradient echo sequence. The gradient echo sequence can be what is known as a TrueFISP sequence, and this corresponds to a gradient echo sequence with completely rephased gradients in all spatial directions. The records in step S21 may be ECG triggered, or the images are recorded continuously and the images are retrospectively allocated to the cardiac phases by analysis of the image contents. To suppress the respiratory movement, the recording in step S21 can be made using the breath-hold technique. Of course other imaging sequences may also be used that are suitable for generating MR images on which the movement of the myocardium in the time curve can be seen. The MR images recorded in step S21 can be recorded in a single slice, or a number of slices along the short heart axis can be recorded. One parameter of the cardiac geometry is identified in step S22 in the sequence over time of the MR images, for example by segmenting algorithms. One possible parameter of the cardiac geometry is the endocardial contour of the myocardium. Alternatively this may be the epicardial contour of the myocardium, the myocardium volume or the blood volume enclosed by the myocardium. One or more of these parameter(s) can be identified in each of the recorded MR images. The time curve of the identified parameter(s) is determined in a step S23, as is shown inter alia in FIGS. 4 and 5, and this will be described in detail below. The time curve will be determined for one cardiac cycle here.

If the time curve over the cardiac cycle is known then it is possible to determine the mean of the identified parameter, such as the mean of the position of the endocardial contour, the epicardial contour or the myocardium volume (step S24). Since means of the movement are being used, this results in as much expansion as compression of the myocardium. The error that would occur in the case of diffusion measurements therefore balances itself out or is neutralized using these means. It is therefore possible in step S25 to switch the diffusion gradients, which are switched in different variations and directions in the case of diffusion tensor imaging, during subsequent diffusion measurements at the point-in-times pertaining to the determined means, or at one of the associated point-in-times, in order to determine the diffusion tensor. The diffusion gradients can by way of example be centrally arranged around the determined measuring point-in-times, or the measuring point-in-times are the trigger point-in-time for starting the additional diffusion gradients.

The method ends in step S26.

FIGS. 4A-4F show the different time curves for different parameters standardized over the cardiac cycle in the time curve. A gradient echo sequence with completely refocused magnetic field gradients was used as the imaging sequence, with the time resolution for creating an MR image being about 40 ms. Curve 41 illustrates the absolute shift of the epicontour of the myocardium for six different layers of the short cardiac axis, whereas curve 42 illustrates the radial shift of the epicardial contour, averaged over the azimuth, for six different layers. Curves 43 and 44 each illustrate the absolute shift of the endocardial contour (curve 43) or the radial shift of the endocardial contour (curve 44). Curves 45 and 46 illustrate the absolute or radial shift of the myocardium volume from measurements on test persons. As may be seen from these curves, the measurement begins in each case in the diastole with a relaxed heart muscle, and as may be seen in the curves, the contraction and the subsequent relaxation then occur.

Since the time curve is standardized to one cardiac cycle the values lie between 0 and 1 on the time axis.

Figure 5:
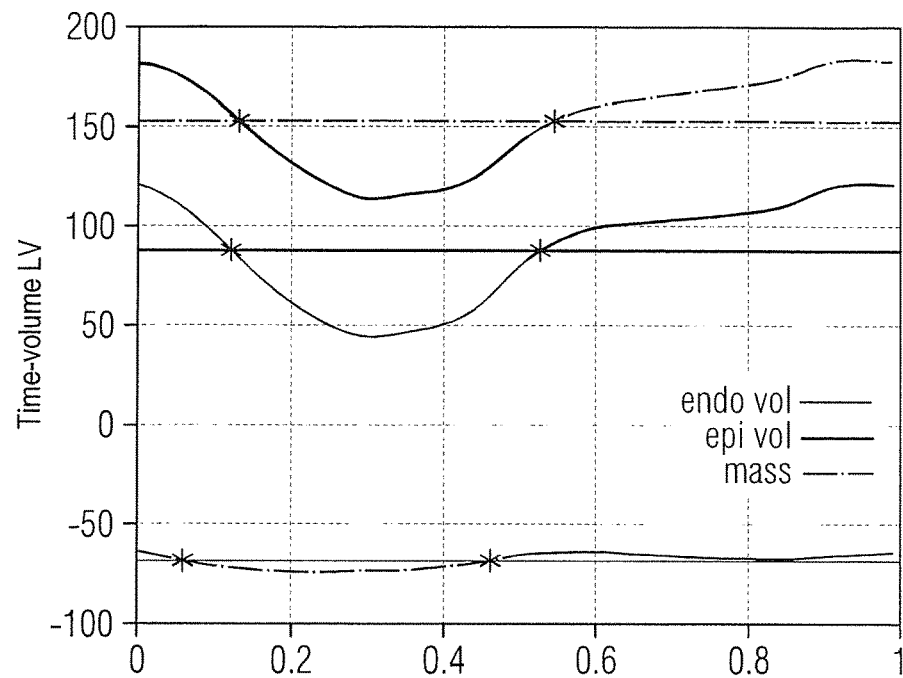
FIG. 5 shows the time curve of the blood volume in the left ventricle for comparison.

FIG. 5 also shows the time curve of the determined endocardial volume and the epicardial volume and the myocardium volume respectively, either the entire volume of the ventricle or that present in the measured layer. The bottom curve in FIG. 5 is the difference between the two top curves and corresponds to the myocardium volume. Theoretically the contour length is most similar to the mean deformation in the center of the myocardium (i.e. approximately the mean of epi- and endocontours), although all of these parameters produce similar sweet spot positions. Measurements based on the endocontour are advantageous since the endocontour can be determined more reliably than the epicontour.

With reference to FIG. 3 it will now be described in detail how measuring point-in-times or sweet spots can be identified from the time curves illustrated in FIGS. 4 and 5. Step S24, which was mentioned in FIG. 2, can be carried out in detail as follows.

The start value of the parameter at the beginning of the cardiac cycle is added at the end again in the time curve in a step S241, so the curves start and end with the same value. The time resolution is increased by interpolation in a step S242. The time resolution of an MR image can be about 40 ms, and this means that there is a determined parameter value every 40 ms in FIGS. 4 and 5. The time resolution can be increased by way of interpolation, for example Fourier interpolation, so there are parameter values every 5 ms or 10 ms by way of example. The parameter value added in step S241 at the end of the cardiac cycle can be removed again in step S243 before the arithmetic mean of the individual parameter values is formed in step S244. In this connection values obtained by way of interpolation can be taken into account when forming the arithmetic mean.

Figure 6:
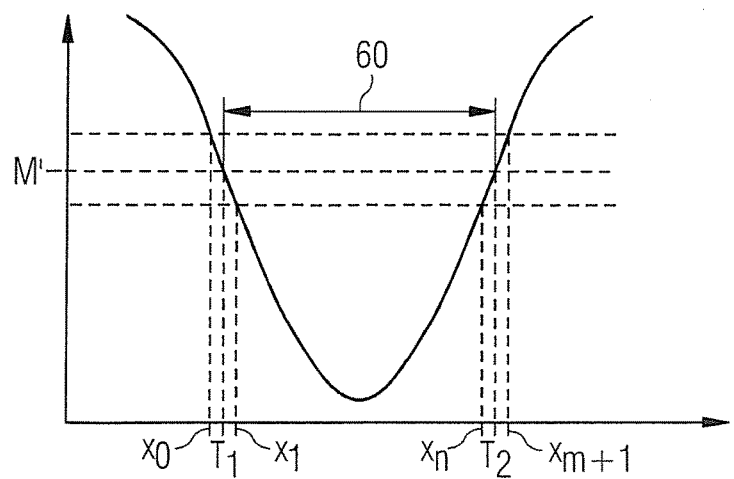
FIG. 6 schematically shows how the measuring point-in-times are determined from the time curve.

As may be seen in the curves in FIGS. 4 and 5, the volume at the beginning and end of the measurement is always greater than the mean. Since there is only one contraction per cardiac cycle and the parameter values form a continuous curve, all parameter values which are less than the arithmetic mean can be identified in a step S245. With reference to FIG. 6 this means that all parameter values within the period 60 are identified. The first parameter value within this period 60 can then be identified in a step S246: in the illustrated example of FIG. 6 the parameter value which was determined at the first point-in-time X1. The first parameter value X0 directly therebefore is likewise determined. Since X1, the first parameter value, is less than the mean, the parameter value at point-in-time X0 is inevitably greater than the mean. The first measuring point-in-time for the diffusion measurements accordingly lies between the first point-in-times X0 and X1. If a linear interpolation occurs between the parameter values at point-in-time X0 and X1, it can be determined at which measuring point-in-time T1 the curve corresponds to the arithmetic mean of the parameter, namely M'. The present method is based on the fact that all deformation components proceed synchronously. This means that it is sufficient to measure just one of the components, by way of example the radial component. This is the case irrespective of the symmetry of the movement. If a parameter is then measured which is quadratically connected to a deformation component, such as the volume of the myocardium, then the positions of the means over time only match the positions of the deformation means well if the movement relative to this point-in-time is approximately symmetrical. In addition, however, the deformation proceeds approximately linearly to the change in volume. There is an offset between the information of the contour length and the deformation because the distortion is on average 0, i.e. with distortion 0 the contour length is >0 and the volume >0. With mean distortion values the myocardium has a volume V. With a maximum deformation value it has a volume V−v, with the minimum deformation it has the value V+v. Since v is much smaller than V, the relationship in the assumed deformation value range is approximately linear.

With reference once again to FIG. 3, linear interpolation follows in step S247, resulting in the first measuring point-in-time T1. This measuring point-in-time T1 can then be used for diffusion encoding for the diffusion measurements.

Identification of the last parameter value within the period 60, namely of the parameter value at point-in-time XN, also occurs in step S248. This is the last parameter value which is smaller than the mean, so the following parameter value XN+1, which can be an interpolated value, is greater than the mean. The second point-in-times, the second measuring point-in-time T2, at which the encoding for the diffusion measurements can be carried out can in turn be identified by linear interpolation between XN and XN+1. The interpolation in step S249 therefore leads to the second measuring point-in-time T2.

If the movement of the myocardium relative to the mean is symmetrical to the mean, the measuring point-in-times T1 or T2 can be determined if just the radial deformation component is used. The radial shift of the inner myocardium wall is, as described above, proportional to the change in blood volume within this layer. Of interest to the diffusion, however, is the radial deformation of the myocardium tissue between the inner and outer myocardium walls, i.e. between the endocardial and epicardial contours. Since, as shown in FIGS. 4 and 5, the radial shift of the inner or outer wall produces substantially the same measuring point-in-times as T1 or T2, this also then applies to the tissue within these boundaries. The time curve of the blood volume is consequently a good measure of the measuring point-in-times or sweet spots.

As may be seen in FIGS. 4 and 5, the determined means are very similar for different short-axis positions. This means that it is not necessary to determine the mean or means separately for each layer of a time volume curve of the blood volume. Instead it is possible to use a single global time-volume curve, namely one of the curves shown in FIG. 4 or 5, in order to determine the sweet spots.

The present invention accelerates the preparation phase for diffusion measurements in the heart. No additional measurements are necessary. A deformation calculation does not have to be carried out. Furthermore, since the measuring point-in-times, such as the point-in-times T1 and T2, can be determined automatically, a manual adjustment of the diffusion measurements for switching the diffusion gradients is not necessary. The sweet spot values generated in this way can then automatically be used for the diffusion measurements, for example in the case of DTST measurements (double triggered stimulated echo preparation), such as by using an application that allows the information generated during an examination to be transferred to subsequent MR measurements. User interaction for scheduling the measurement is not necessary here. The results of the analysis mentioned above, i.e. determining the sweet spot positions, can be used as follows: one possibility consists in presenting the sweet spot values to the operator of the system, for example in the form of a table and possibly with alternatives based on the evaluation alternatives, such as the blood volume over contour length or volume value over different layers, at the end of the recording of the plurality of MR images, i.e. the cine measurements. The values can also be displayed together with quality information such as error bars, which are estimated from the values obtained in different ways, or with the intermediate results of the evaluation, such as contours and curves. It is also possible to transfer the information generated during an examination to subsequent measuring steps. Therefore, for example, slice positions and orientations found by analysis of overview images can be automatically transferred to the subsequent clinical measurements. With diffusion measurements the sweet spot parameter must be stored in the MR system and the diffusion measurement protocol must be configured such that this information is automatically loaded before the start or scheduling. User interactions for choosing between, for example T1 and T2 or the decision between alternatives can then be offered in the application protocol if the choice has not been automatically made beforehand. The determined measuring point-in-times T1 or T2 may also be used. The greater the gradient of the parameter curve is in the measuring point-in-time, the greater the effect of an error in the sweet spot determination is on the diffusion measurement. The sweet spot with the lower gradient is advantageous assuming that T1 and T2 are determined with the same level of accuracy.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for determining at least one point-in-time within a cardiac cycle at which a magnetic resonance (MR) at which diffusion data from the myocardium of an examination subject are to be acquired, said method comprising:
    operating an MR data acquisition unit, while an examination subject is situated therein, to acquire a sequence of MR images of the heart of the examination subject, said heart exhibiting a geometric feature represented in said MR images that is a length or a volume associated with a selected contour of the heart;
    providing said MR images to a computer and, in said computer, automatically determining a time curve of a parameter of said geometric feature in said sequence, said time curve representing changing of said parameter within each cardiac cycle due to beating of said heart;
    in said computer, automatically determining a mean of said parameter from said time curve, and then determining a point in time along said time curve at which said mean occurs;
    emitting an electronic control signal from said computer to said MR data acquisition unit that identifies said point in time at which said mean occurs, as a designation of at least one point-in-time that said MR diffusion data of the myocardium should be acquired, and said MR data acquisition unit responding to said electronic control signal to acquire said MR diffusion data of the myocardium at said at least one point-in-time; and
    in said computer, transforming the acquired MR diffusion data of the myocardium into image data, and making the image data available in electronic form, as a data file, from said computer.

2. A method as claimed in claim 1 comprising, in said computer, determining a parameter value of said parameter in each of said MR images in said sequence and determining, as said mean, the arithmetic mean of said parameter values, and designating a point-in-time in said electrical signal from said computer, at which said arithmetic mean occurs on said time curve, as said point-in-time at which said MR diffusion data of the myocardium should be acquired.

3. A method as claimed in claim 2 comprising, in said computer:
    identifying a period within said time curve of said parameter within which all parameter values of said parameter are less than said arithmetic mean;
    determining a first-occurring parameter value in said period and determining a preceding parameter value that occurs immediately before said first-occurring parameter value in said time curve;
    identifying a first point in time that is between respective points in time at which said first-occurring parameter value and said preceding parameter value occur;
    identifying a last-occurring parameter value within said period and a next parameter value that occurs immediately after said last-occurring parameter value;
    identifying a second point-in-time in said time curve that is between points-in-time in said time curve at which said last-occurring parameter value and said next parameter value occur; and
    emitting said first point-in-time and said second point-in-time from said computer as electronic signals that each designate a point-in-time at which said MR diffusion data of the myocardium should be acquired.

4. A method as claimed in claim 3 comprising determining said first point-in-time using a linear interpolation between said preceding parameter value and said first-occurring parameter value, and determining said second point-in-time using a linear interpolation between said last-occurring parameter value and said next parameter value.

5. A method as claimed in claim 1 comprising using, as said parameter of said geometric feature, a parameter selected from the group consisting of the endocardial contour of the myocardium, the epicardial contour of the myocardium, and the volume of the myocardium.

6. A method as claimed in claim 1 comprising operating said MR data acquisition unit to acquire said sequence of MR images with a gradient echo sequence in which magnetic field gradients are all completely refocused.

7. A method as claimed in claim 1 comprising determining said time curve of said parameter by identifying respective parameter values of said parameter in each of said MR images in said sequence, with each MR image in said sequence being situated in a single imaging layer of the heart of the examination subject.

8. A method as claimed in claim 1 comprising, in said computer:
    determining said parameter by identifying a respective parameter value of said parameter in each of said MR images in said sequence; and
    determining said time curve of said parameter by interpolating between the respective parameter values, and before said interpolation, adding a first-occurring parameter value at an end of the cardiac cycle, thereby causing said time curve to begin and end at equal parameter values.

9. A method as claimed in claim 8 comprising removing said added parameter value at said end of the cardiac cycle when determining said mean.

10. A method as claimed in claim 1 comprising implementing said acquisition of MR diffusion data from the myocardium at said point in time by operating said MR data acquisition unit to activate at least one diffusion gradient that encodes said MR data acquired from the myocardium at said point in time.

11. A magnetic resonance (MR) apparatus comprising:
an MR data acquisition unit;
a computer configured to operate the MR data acquisition unit, while an examination subject is situated therein, to acquire a sequence of MR images of the heart of the examination subject, said heart exhibiting a geometric feature represented in said MR images that is a length or a volume associated with a selected contour of the heart;
said computer being configured to automatically determine a time curve of a parameter of said geometric feature in said sequence, said parameter changing within each cardiac cycle due to beating of said heart;
said computer being configured to automatically determine a mean of said parameter from said time curve, and then determine a point in time along said time curve at which said mean occurs;
said computer being configured to emit an electronic signal from said computer that identifies said point in time at which said mean occurs, as a designation of at least one point-in-time that said MR data acquisition unit should be operated to acquire MR diffusion data of the myocardium of the examination subject, and said MR data acquisition unit responding to said electronic control signal to acquire said MR diffusion data of the myocardium at said at least one point-in-time; and
said computer being configured to transform the acquired MR diffusion data of the myocardium into image data, and to make the image data available in electronic form, as a data file, from said computer.

12. A non-transitory, computer-readable data storage medium encoded with programming instructions, said storage medium being loaded into a control and processing computer system of a magnetic resonance (MR) apparatus, said MR apparatus also comprising an MR data acquisition unit, and said programming instructions causing said control and processing computer system to:
operate the MR data acquisition unit, while an examination subject is situated therein, to acquire a sequence of MR images of the heart of the examination subject, said heart exhibiting a geometric feature represented in said MR images that is a length or a volume associated with a selected contour of the heart;
automatically determine a time curve of a parameter of said geometric feature in said sequence, said parameter changing within each cardiac cycle due to beating of said heart;
automatically determine a mean of said parameter from said time curve, and then determine a point in time along said time curve at which said mean occurs;
emit an electronic signal that identifies said point in time at which said mean occurs, as a designation of at least one point-in-time that said MR data acquisition unit should be operated to acquire MR diffusion data of the myocardium of the examination subject, in order to cause said MR data acquisition unit to respond to said electronic control signal to acquire said MR diffusion data of the myocardium at said at least one point-in-time; and
transform the acquired MR diffusion data of the myocardium into image data, and make the image data available in electronic form, as a data file, from said computer.

* * * * *